United States Patent
Westlund

(10) Patent No.: US 12,233,259 B2
(45) Date of Patent: Feb. 25, 2025

(54) TRANSVASCULAR MEDICAL LEAD

(71) Applicant: ZOLL RESPICARDIA, INC., Minnetonka, MN (US)

(72) Inventor: Randy W. Westlund, St. Paul, MN (US)

(73) Assignee: ZOLL RESPICARDIA, INC., Minnetonka, MN (US)

( * ) Notice: Subject to any disclaimer, the term of this patent is extended or adjusted under 35 U.S.C. 154(b) by 0 days.

(21) Appl. No.: 18/520,837

(22) Filed: Nov. 28, 2023

(65) Prior Publication Data

US 2024/0165404 A1    May 23, 2024

Related U.S. Application Data

(63) Continuation of application No. 17/843,014, filed on Jun. 17, 2022, now Pat. No. 11,865,333, which is a continuation of application No. 16/716,777, filed on Dec. 17, 2019, now Pat. No. 11,389,648, which is a continuation of application No. 14/934,869, filed on Nov. 6, 2015, now Pat. No. 10,543,363, which is a continuation of application No. 12/330,095, filed on Dec. 8, 2008, now Pat. No. 9,199,075.

(60) Provisional application No. 61/063,960, filed on Feb. 7, 2008.

(51) Int. Cl.
| | |
|---|---|
| *A61N 1/05* | (2006.01) |
| *A61N 1/36* | (2006.01) |
| *A61N 1/365* | (2006.01) |
| *A61N 1/37* | (2006.01) |

(52) U.S. Cl.
CPC .............. *A61N 1/056* (2013.01); *A61N 1/05* (2013.01); *A61N 1/0558* (2013.01); *A61N 1/3611* (2013.01); *A61N 1/36139* (2013.01); *A61N 1/36521* (2013.01); *A61N 1/36542* (2013.01); *A61N 1/37* (2013.01); *A61N 1/0551* (2013.01); *A61N 2001/0585* (2013.01)

(58) Field of Classification Search
CPC ......... A61N 1/056; A61N 1/05; A61N 1/0558
See application file for complete search history.

(56) References Cited

U.S. PATENT DOCUMENTS

| | | |
|---|---|---|
| 4,129,125 A | 12/1978 | Lester et al. |
| 4,209,019 A | 6/1980 | Dutcher et al. |
| 4,702,253 A | 10/1987 | Nappholz et al. |
| 4,827,935 A | 5/1989 | Geddes et al. |
| 4,830,008 A | 5/1989 | Meer |
| 5,002,067 A | 3/1991 | Berthelsen et al. |
| 5,056,519 A | 10/1991 | Vince |

(Continued)

FOREIGN PATENT DOCUMENTS

| | | |
|---|---|---|
| DE | 10103288 A1 | 8/2002 |
| WO | 2008092246 A1 | 8/2008 |

OTHER PUBLICATIONS

Aiyar, Harish et al., Diaphragm Pacing for Chronic Respiratory Insufficiency, CRC Press, LLC, 2001, Chapter 9.

(Continued)

*Primary Examiner* — Paula J Stice
(74) *Attorney, Agent, or Firm* — Lando & Anastasi, LLP

(57) ABSTRACT

A medical electrical lead and methods of implanting medical electrical leads in lumens. Leads in accordance with the invention employ preformed biases to stabilize the lead within a lumen or lumen and to provide feedback to lead implanters.

15 Claims, 7 Drawing Sheets

(56) References Cited

U.S. PATENT DOCUMENTS

| | | |
|---|---|---|
| 5,146,918 A | 9/1992 | Kallok et al. |
| 5,170,802 A | 12/1992 | Mehra |
| 5,199,428 A | 4/1993 | Obel et al. |
| 5,265,604 A | 11/1993 | Vince |
| 5,330,507 A | 7/1994 | Schwartz |
| 5,423,865 A * | 6/1995 | Bowald ............. A61N 1/3918 607/126 |
| 5,483,969 A | 1/1996 | Testerman et al. |
| 5,485,851 A | 1/1996 | Erickson |
| 5,524,632 A | 6/1996 | Stein et al. |
| 5,578,061 A | 11/1996 | Stroetmann et al. |
| 5,800,470 A | 9/1998 | Stein et al. |
| 5,922,014 A | 7/1999 | Warman et al. |
| 5,938,694 A | 8/1999 | Jaraczewski et al. |
| 6,006,134 A | 12/1999 | Hill et al. |
| 6,132,384 A | 10/2000 | Christopherson et al. |
| 6,212,434 B1 * | 4/2001 | Scheiner ............. A61N 1/0563 607/123 |
| 6,212,435 B1 | 4/2001 | Lattner et al. |
| 6,266,564 B1 | 7/2001 | Hill et al. |
| 6,314,324 B1 | 11/2001 | Lattner et al. |
| 6,360,740 B1 | 3/2002 | Ward et al. |
| 6,415,183 B1 | 7/2002 | Scheiner et al. |
| 6,449,507 B1 | 9/2002 | Hill et al. |
| 6,463,327 B1 | 10/2002 | Lurie et al. |
| 6,532,388 B1 | 3/2003 | Hill et al. |
| 6,537,228 B1 | 3/2003 | Lambert |
| 6,542,774 B2 | 4/2003 | Hill et al. |
| 6,587,726 B2 | 7/2003 | Lurie et al. |
| 6,641,542 B2 | 11/2003 | Cho et al. |
| 6,684,101 B2 | 1/2004 | Daum |
| 6,718,208 B2 | 4/2004 | Hill et al. |
| RE38,705 E | 2/2005 | Hill et al. |
| 6,881,192 B1 | 4/2005 | Park |
| 6,890,306 B2 | 5/2005 | Poezevera |
| 6,928,324 B2 | 8/2005 | Park et al. |
| 6,934,583 B2 | 8/2005 | Weinberg et al. |
| 6,937,903 B2 | 8/2005 | Schuler et al. |
| 6,964,641 B2 | 11/2005 | Cho et al. |
| 7,025,730 B2 | 4/2006 | Cho et al. |
| 7,070,568 B1 | 7/2006 | Koh |
| 7,077,132 B2 | 7/2006 | Berthon-Jones |
| 7,082,331 B1 | 7/2006 | Park et al. |
| 7,094,207 B1 | 8/2006 | Koh |
| 7,155,278 B2 | 12/2006 | King et al. |
| 7,179,229 B1 | 2/2007 | Koh |
| 7,184,829 B2 | 2/2007 | Hill et al. |
| 7,200,442 B1 | 4/2007 | Koh et al. |
| 7,212,862 B2 | 5/2007 | Park et al. |
| 7,223,244 B1 | 5/2007 | Koh |
| 7,225,019 B2 | 5/2007 | Jahns et al. |
| 7,225,021 B1 | 5/2007 | Park et al. |
| 7,245,971 B2 | 7/2007 | Park et al. |
| 7,269,457 B2 | 9/2007 | Shafer et al. |
| 7,269,459 B1 | 9/2007 | Koh |
| 7,277,757 B2 | 10/2007 | Casavant et al. |
| 7,340,302 B1 | 3/2008 | Falkenberg et al. |
| 7,357,775 B1 | 4/2008 | Koh |
| 7,361,146 B1 | 4/2008 | Bharmi et al. |
| 7,363,086 B1 | 4/2008 | Koh et al. |
| 7,371,220 B1 | 5/2008 | Koh et al. |
| 7,676,275 B1 | 3/2010 | Farazi et al. |
| 7,813,805 B1 | 10/2010 | Farazi |
| 9,199,075 B1 | 12/2015 | Westlund |
| 10,543,363 B2 | 1/2020 | Westlund |
| 2001/0003799 A1 | 6/2001 | Boveja |
| 2002/0049479 A1 | 4/2002 | Pitts |
| 2002/0128563 A1 | 9/2002 | Carlson et al. |
| 2003/0078623 A1 | 4/2003 | Weinberg et al. |
| 2003/0088244 A1 | 5/2003 | Swanson et al. |
| 2003/0195571 A1 | 10/2003 | Burnes et al. |
| 2005/0043765 A1 | 2/2005 | Williams et al. |
| 2005/0085734 A1 | 4/2005 | Tehrani |
| 2005/0085865 A1 | 4/2005 | Tehrani |
| 2005/0085866 A1 | 4/2005 | Tehrani |
| 2005/0085867 A1 | 4/2005 | Tehrani et al. |
| 2005/0085868 A1 | 4/2005 | Tehrani et al. |
| 2005/0085869 A1 | 4/2005 | Tehrani et al. |
| 2005/0165457 A1 | 7/2005 | Benser et al. |
| 2005/0197588 A1 | 9/2005 | Freeberg |
| 2005/0240240 A1 | 10/2005 | Park et al. |
| 2005/0288729 A1 | 12/2005 | Libbus et al. |
| 2006/0030894 A1 | 2/2006 | Tehrani |
| 2006/0036294 A1 | 2/2006 | Tehrani |
| 2006/0122662 A1 | 6/2006 | Tehrani et al. |
| 2006/0142815 A1 | 6/2006 | Tehrani et al. |
| 2006/0149334 A1 | 7/2006 | Tehrani et al. |
| 2006/0155341 A1 | 7/2006 | Tehrani et al. |
| 2006/0167523 A1 | 7/2006 | Tehrani et al. |
| 2006/0184060 A1 | 8/2006 | Belalcazar et al. |
| 2006/0229677 A1 | 10/2006 | Moffitt et al. |
| 2006/0247729 A1 | 11/2006 | Tehrani et al. |
| 2007/0021795 A1 | 1/2007 | Tehrani |
| 2007/0118183 A1 | 5/2007 | Gelfand et al. |
| 2007/0156199 A1 | 7/2007 | Koh et al. |
| 2007/0260285 A1 | 11/2007 | Libbus et al. |
| 2007/0288076 A1 * | 12/2007 | Bulkes ............. A61N 1/37211 607/116 |
| 2007/0293895 A1 | 12/2007 | Cowan et al. |
| 2008/0097566 A1 * | 4/2008 | Colliou ............. A61N 1/056 607/122 |
| 2008/0132983 A1 * | 6/2008 | Cohen ............. A61N 1/36114 607/118 |
| 2008/0154330 A1 | 6/2008 | Tehrani et al. |
| 2008/0161878 A1 | 7/2008 | Tehrani et al. |
| 2008/0167695 A1 | 7/2008 | Tehrani et al. |
| 2008/0177347 A1 | 7/2008 | Tehrani et al. |
| 2008/0183239 A1 | 7/2008 | Tehrani et al. |
| 2008/0183240 A1 | 7/2008 | Tehrani et al. |
| 2008/0183254 A1 | 7/2008 | Bly et al. |
| 2008/0183259 A1 | 7/2008 | Bly et al. |
| 2008/0183264 A1 | 7/2008 | Bly et al. |
| 2008/0188903 A1 | 8/2008 | Tehrani et al. |
| 2008/0188904 A1 | 8/2008 | Tehrani et al. |
| 2008/0234694 A1 | 9/2008 | Stegfeldt et al. |
| 2009/0088827 A1 | 4/2009 | Tockman et al. |
| 2010/0249630 A1 | 9/2010 | Droitcour et al. |
| 2011/0060380 A1 | 3/2011 | Gelfand et al. |
| 2020/0121922 A1 | 4/2020 | Westlund |
| 2022/0370790 A1 | 11/2022 | Westlund |

OTHER PUBLICATIONS

Anatomy AtlasesTM http://www.anatomyatlases.org/AnatomicVariants/Cardiovascular/Text/Arterier/Heart.shtml © 1995-2016 the Author(s) and Michael P. D'Alessandro, M.D. [downloaded Feb. 19, 2016].

Arzt, Michael et al., Treatment of Sleep Apnea in Heart Failure, Am J Respir Crit Care Med vol. 173, pp. 1300-1308, 2006.

Bilgutay, A.M. et al., Augmented Ventilation by Synchronous Phrenic Nerve Stimulation, Trans. Amer. Soc. Artif. Int. Organs, 1970, vol. XVI, pp. 213-217.

Brack, Thomas, Cheyne-Stokes Respiration in Patients with Congestive Heart Failure, Seiss Med Wkly 2003; 133:605-610, www.smw.ch.

Caples, Sean M. et al., Influence of Cardiac Function and Failure on Sleep-Disordered Breathing, Journal of Applied Physiology 2005, vol. 99, pp. 2433-2439.

Chatfield, Paul O. et al., Role of Pulmonary Proprioceptive Reflexes in Suppression of Spontaneous Breathing During Electophrenic Respiration, Dept. of Physiology, Harvard Medical School, and Dept. of Physiology, Harvard School of Public Health, vol. 163, Oct. 1950.

Diedrichs, Holger et al., Symptomatic Relief Precedes Improvement of Myocardial Blood Flow in Patients Under Spinal Cord Stimulation, BioMed Central, 2005, pp. 1-7.

Dobelle, William H., Use of Breathing Pacemakers to Suppress Intractable Hiccups of up to Thirteen Years Duration, ASAIO Journal 1999, pp. 524-525.

Echo Pedia.org http://www.echopedia.org/index.php/Normal_Values_of_TEE; page was last modified on Jan. 7, 2012 [downloaded Feb. 19, 2016].

(56) References Cited

OTHER PUBLICATIONS

Escher, Doris J.W., Clinical control of Respiration by Transvenous Phrenic Pacing, Trans. Amer. Soc. Artif. Int. Organs., vol. XIV, 1968.
Esler, Murray et al., Is Obstructive Sleep Apnea the Cause of Sympathetic Nervous Activation in Human Obesity?, Journal of Applied Physiology 2006, vol. 100, pp. 11-12.
Furman, Seymour, MD et al., Transvenous Stimulation of the Phrenic Nerves, Journal of Thoracic and Cardiovascular Surgery, vol. 62, No. 5, 1971, pp. 743-751.
Garrido-Garcia, H. et al., Treatment of Chronic Ventilatory Failure Using a Diaphragmatic Pacemaker, Spinal Cord (1998) 36, 310-314.
Gottfried, Stewart B. et al., Effects of Phrenic Stimulation on Upper Airway Resistance in Anesthetized Dogs, Am Physiological Society 1983, 0161-7567/83, pp. 419-426.
Hall, Michael J. et al., Cycle Length of Periodic Breathing in Patients with and without Heart Failure, Am. J. Respir. Crit. Care Med vol. 154, pp. 376-381, 1996.
Handa, Y. et al., Basic Studies on Electrophrenic Respiration Pat 2-Assisted Ventilation by the Synchronous Electrophrenic Respirator, Medical and Biological Engineering, Jul. 1976.
Hasdemir, Can MD et al., Jpn Heart J, vol. 44 No. 3, 2003.
Ishii, Kiyoshi, Effects of Bilateral transvenous diaphrahm pacing on hemodynamic function in patients after cardiac operations. 1990.
Javaheri, Shahrokh M.D., CPAP Should Not Be Used for Central Sleep Apnea in Congestive Heart Failure Patients, Journal of Clinical Sleep Medicine, vol. 2, No. 4, 2006.
Javaheri, Shahrokh, MD, Acetazolamide Improves Central Sleep Apnea in Heart Failure Pulmonary Service, Department of Veterans Affairs Medical Center, and Department of Medicine, University of Cincinnati College of Medicine, Cincinnati, Ohio Am J Respir Crit Care Med vol. 173. pp. 234-237, 2006, Jul. 5, 2005.
Javaheri, Shahrokh, MD, Central Sleep Apnea in Congestive Heart Failure: Prevalence, Mechanisms, Impact, and Therapeutic Options, Seminars in Respiratory and Critical Care Medicine, 2005, vol. 26, No. 1.
Kaneko, S. et al., A New Approach to Respiratory Assist for Phrenic Nerve Paralysis, Trans Am Soc. Artif Intern Organs, 1985, vol. XXXI, pp. 301-304.
Kimura, M. et al., A Heart-Rate-Responsive Diaphragm Pacemaker, Med. & Biol. Eng. & Comput., 1987, 25, 458-462.
Kimura, M. et al., Addition to an RF-Coupled Phrenic Nerve Stimulator Implant to Provide Outward Transmission of Body Temperature, Med. & Biol. Eng. & Comput. 1986, 24, 659-661.
Kimura, M. et al., Heart Rate and Body Temperature Sensitive Diaphragm Pacing, Med. & Biol. Eng. & Comput. 1992, 30, 155-16.
Kingma, John G. Jr. et al., Nueromodulation Therapy Does Not Influence Blood Flow Distribution or Left-Ventricular Dynamics During Acute Myocardial Ischemia, Autonomic Neuroscience; Basic and Clinical 91 (2001) pp. 47-54.
Kohnlein, T. et al., Central Sleep Apnea Syndrome in Patients with Chronic Heart Disease: A Critical Review of the Current Literature, Thoarx 2002; 57:547-554.
Leuenberger, URS A. et al., Hypoxia Augments Apnea-Induced Peripheral Vasoconstriction in Humans, Journal of Applied Physiology 2001, vol. 90, pp. 1516-1522.
Leung, Richard s. T. et al., Influence of Cheyne-Stokes Respiration on Cardiovascular Oscillations in Heart Failure, Am J Respir Crit Care Med , 2003, vol. 167. pp 1534-1539.
Levy, T. et al., A Comparison Between Passive and Active Fixation Leads in the in the Coronary Sinus for Biatrial Pacing, The European Society of Cardiology 2000.
Linderoth, Bengt, Md, Pho et al., Mechanisms of Spinal Cord Stimulation in Painful Syndromes: Role of Animals Models, American Academy of Pain Medicine, vol. 7, No. SI4-S26, 2006.
Lorenzi-Filho, Geraldo et al., Cheyne-Stokes Respiration in Patients with Congestive Heart Failure: Causes and Consequences, Clinics 2005; 60(4):333-44.

Macintyre, Neil R., MD, Setting the Frequency-Tidal Volume Pattern, www.rcjournal.com/contents/03.02/03.02.0266.asp [retrieved from the Internet on Sep. 11, 2006].
Oliven, Arie et al., Upper Airway Response to Electrical Stimulation of the Genioglossus in Obstructive Sleep Apnea, Journal of Applied Physiology, 95:2023-2029, 2003.
Parati, Gianfranco et al., Sleep Apnea: Epidemiology, Pathophysiology, and Relation to Cardiovascular Risk, Am Journal Physiological Society 2007, vol. 293, pp. RI671-RI683.
Planas, Roque F. et al., Diaphragmatic Pressures: Transvenous vs. Direct Phrenic Nerve Stimulation, Am Physiological Society 1985, 0161-7567/85, pp. 269-273.
Plisiene, Jurgita et al., Selective Transvascular Stimulation of Cardiac Autonomic Nerves: A Novel Technique, Biomedicine vol. 2 No. 1, Jul. 2002.
Prosecution hisory from corresponding U.S. Appl. No. 12/330,095, filed Dec. 8, 2008 including: Notice of Allowance mailed Jul. 30, 2015; Final Rejection mailed Apr. 27, 2015; Non-Final Rejection mailed Sep. 4, 2014; Non-Final Rejection mailed Jan. 7, 2014; Final Rejection mailed Jun. 11, 2013; Non-Final Rejection mailed Aug. 21, 2012; Final Rejection mailed Sep. 30, 2011; and Non-Final Rejection mailed Feb. 17, 2011.
Prosecution history from corresponding U.S. Appl. No. 14/934,869, filed Nov. 6, 2015 including: Notice of Allowance mailed Sep. 17, 2019; Final Rejection mailed Jun. 13, 2019, Non-Final Rejection mailed Sep. 27. 2018; Final rejection mailed Dec. 11, 2017; Non-Final Rejection mailed Mar. 31, 2017; Final Rejection mailed Sep. 12, 2016; and Non-Final Rejection mailed Feb. 23, 2016.
Punjabi, Naresh M. et al., Disorders of Glucose Metabolism in Sleep Apnea, Journal of Applied Physiology 2005, vol. 99, pp. 1998-2007.
Redline, Susan et al., Beyond the Fat Boy, Journal of Applied Physiology 2005, vol. 99: pp. 1243-1244.
Sarnoff, Stanley J. et al., Electrophrenic Respiration IV. The Effectiveness of Contralateral Ventilation During Activity of One Phrenic Nerve, Dept. of Physiology, Harvard School of Public Health, 1949, pp. 929-937.
Sarnoff, Stanley J. et al., Electrophrenic Respiration. III. Mechanism of the Inhibition of Spontaneous Respiration, Dept. of Physiology, Harvard School of Public Health, 1948, vol. 155, pp. 203-207.
Schauerte, Patrick et al., Catheter Stimulation of Cardiac Parasympathetic Nerves in Humans: A Novel Approach to the Cardiac Autonomic Nervous System, American Heart Association 2006.
Series, F. et al., Site of Phrenic Nerve Stimulation-Induced Upper Airway Collapse: Influence of Expiratory Time, Journal of Applied Physiology 2002, vol. 92, pp. 665-671.
Series, Frederic, Assessment of Upper Airway Dynamics in Awake Patients with Sleep Apnea Using Phrenic Nerve Stimulation, Am Journal Respir Crit Care Med, 2000, vol. 162., pp. 795-800.
Shaul, Donald B., et al., Thoracoscopic Placement of Phrenic Nerve Electrodes for Diaphragmatic Pacing in Children, Journal of Pediatric Surgery, vol. 3 7, No. 7 pp. 974-978, 2002.
Stemmer, Edward A. MD et al., Diaphragmatic Pacing in the Treatment of Hypoventilation Syndrome, Journal of Thoracic and Cardiovascular Surgery, vol. 54, No. 5, 196 7, pp. 649-657, Nov. 1967.
Taira, Takaomi, MD, Ph. D et al., Phrenic Nerve Stimulation for Diaphragm Pacing with a Spinal cord Stimulator, Elsevier Science, Surg Neurol, 2003; 59:128-32.
Tanaka, Satoshi et al., Mechanisms of Sustained Cutaneous Vasodilation Induced by Spinal Cord Stimulation, Autonomic Neuroscience: Basic and Clinical 114 (2004) pp. 55-60.
Vaseghi, et al., Beyond Coronary Sinus Angiography: The Value of Coronary Arteriography and Identification of the Pericardiophrenic Vein During Left Ventricular Lead Placement, PACE, 2005, vol. 28.
Yasuma, Fumihiko et al., Eight-Year Follow-Up Study of a Patient with Central Alveolar Hypoventilation Treated with Diaphragm Pacing, Respiration, 1998; 65:313-316.
Yumino, Dai et al., Central Sleep Apnea and Cheyne-Stokes Respiration, Proceedings of the American Thoracic Society, 2008, vol. 5, pp. 226-236.

* cited by examiner

TRANSVASCULAR MEDICAL LEAD

CROSS REFERENCE TO RELATED APPLICATIONS

This application claims priority under 35 U.S.C. § 120 to U.S. application Ser. No. 17/843,014, filed Jun. 17, 2022, titled TRANSVASCULAR MEDICAL LEAD, now U.S. Pat. No. 11,865,333, which claims priority under 35 U.S.C. § 120 to U.S. application Ser. No. 16/716,777, filed Dec. 17, 2019, titled TRANSVASCULAR MEDICAL LEAD, now U.S. Pat. No. 11,389,648, which claims priority under 35 U.S.C. § 120 to U.S. application Ser. No. 14/934,869, filed Nov. 6, 2015, titled TRANSVASCULAR MEDICAL LEAD, now U.S. Pat. No. 10,543,363, which claims priority under 35 U.S.C. § 120 to U.S. application Ser. No. 12/330,095, filed Dec. 8, 2008, titled TRANSVASCULAR MEDICAL LEAD, now U.S. Pat. No. 9,199,075, which claims the priority of U.S. Provisional Application 61/063,960, filed Feb. 7, 2008, entitled Muscle and Nerve Stimulation System, each of which is incorporated by reference in its entirety.

BACKGROUND

Electrical stimulation leads for providing medical therapy are being used in an increasing number of applications. Leads have been implanted in patients' hearts, along the spinal column, and in other locations to deliver appropriate therapy. Increasingly leads are implanted in veins, arteries, or other lumens to stimulate tissue near the lumens.

The implantation of electrical leads in lumens presents opportunities because the leads can be fed into the patient's body and implanted without the surgery necessary to install nerve cuffs and other surgically implanted electrodes. Implanting leads in lumens also reduces the possibility of post-surgical trauma or damage to the tissue being stimulated. Difficulties associated with implanting leads in lumens include issues with lead movement or migration and difficulty orienting the lead and electrodes.

SUMMARY

In one embodiment in accordance with the invention, an elongate medical lead includes a lead body having a proximal portion and a distal portion. The proximal portion of the lead is configured to be connected to an electrical signal generator. The lead further includes a stabilizing section proximate the distal portion. The stabilizing section of this embodiment has a first loop configured to turn in a first direction, a second loop configured to turn in the same direction as the first loop, and a bend between the first and second loops. In some embodiments, the loops are generally coplanar with each other. In other embodiments the loops may be perpendicular to each other or at skew angles to each other. In some embodiments, a preformed bend in the lead assists in orienting the lead at the junction of two lumens or a natural bend or flex point in the lumens.

In another embodiment in accordance with the invention, an elongate medical lead includes a lead body having a proximal portion and a distal portion. The proximal portion of the lead is configured to be connected to an electrical signal generator. The lead further includes a stabilizing section proximate the distal portion. The stabilizing section of this embodiment has a first loop configured to turn in a first direction, a second loop configured to turn in the same direction as the first loop, and a bend between the first and second loops. This embodiment includes an electrode on each of the loops that provide an extended bipole configuration when implanted. In some versions, the lead body forms a lumen through which a guide wire or stylet may pass.

In another embodiment in accordance with the invention an elongate medical lead has a proximal portion, a first distal portion having at least one electrode, and a second distal portion also having at least one electrode. In this embodiment the first distal portion is configured to be retained in a subclavian vein of a patient and the second distal portion is configured to be retained in a brachiocephalic vein of a patient. An electrode on the first distal portion of this embodiment is configured to create an extended bipolar electric field with an electrode on the second distal portion. This electric field may be capable of stimulating a phrenic nerve proximate the junction of the subclavian and brachiocephalic veins. In some embodiments, the first and second distal portions may include loops preformed in the lead body.

Another elongate medical lead in accordance with embodiments of the invention has a proximal end configured to be connected to an implantable medical device and a distal end having at least two electrodes. The distal end of the lead body includes a plurality of loops. In some embodiments some loops are parallel to each other and in the form of a coil.

In yet another embodiment in accordance with the invention, an elongate medical lead has a lead body having a proximal portion, a first distal portion, and a second distal portion. There is a bend formed in the lead body between the first distal portion and the second distal portion of this embodiment. At least one electrode is disposed on each of the first and second distal portions. In some embodiments the first and second distal portions are loops, turning in either the same direction as each other or in an opposite direction. In some embodiments the first and second distal portions together form a plurality of loops that are parallel to each other in the form of a coil.

Another embodiment involves a method of implanting a lead in a lumen. The lead is fed into a lumen to a desired location. The lead has a preformed bias proximate the distal end of the lead. There is a removable guide wire or stylet within the lead, and the bias imparts a shape to the lead and guide wire combination. After being fed to the desired location, the lead is rotated to a point where resistance to rotation caused by the shape increases, and the guide wire or stylet is removed from the lead while the lead is in a position of increased rotational resistance.

DETAILED DESCRIPTION

Figure 1:
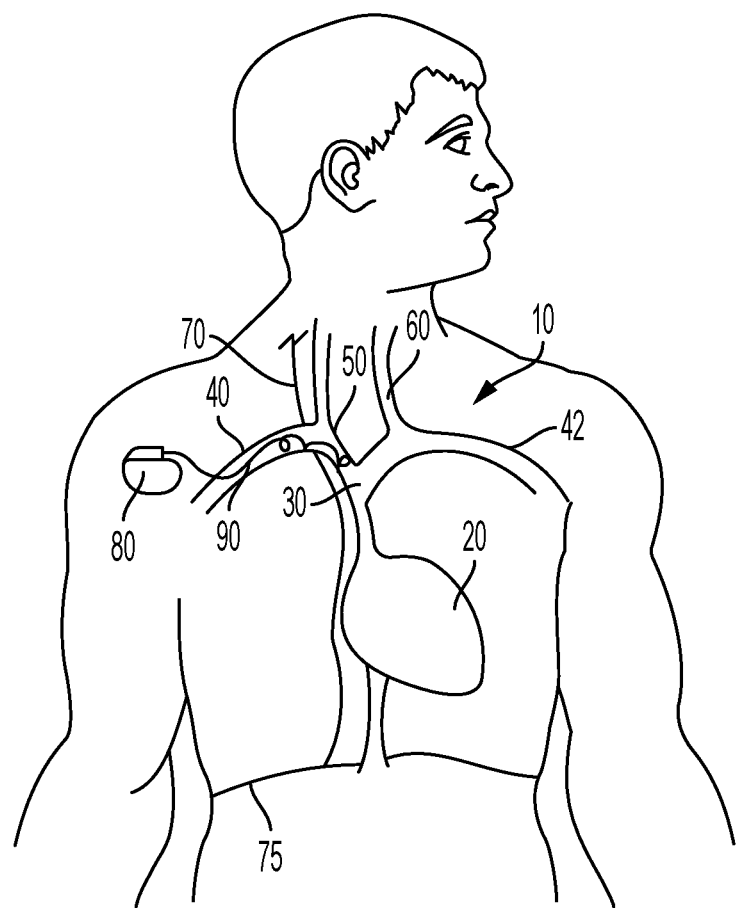
FIG. 1 is a schematic view of a patient with a lead implanted in accordance with embodiments of the invention.

FIG. 1 is a schematic view of a patient with a lead implanted in accordance with embodiments of the invention. FIG. 1 shows relevant elements of the patient's circulatory and nervous system. The displayed portion of the patient's circulatory system 10 includes a heart 20 and a superior vena cava 30 and a right brachiocephalic vein 50 that return blood to the heart from the body. Subclavian veins, including a right subclavian vein 40 (also referred to herein simply as "subclavian vein 40") and a left subclavian vein 42, return blood from the arms and interior jugular veins 60 return blood from the head.

Two phrenic nerves run from a patient's right and left upper spinal column to the right and left hemi-diaphragms and act as the primary motor nerves for each of the hemi-diaphragms, which together make up the diaphragm 75. The right phrenic nerve 70 passes relatively close to the junction of the right brachiocephalic vein 50 and the right subclavian vein 40. The right brachiocephalic vein empties into the superior vena cava 30, which returns blood to the right atrium of the heart 20. The transition from the right brachiocephalic to the superior vena cava is imprecise, and references to the right brachiocephalic vein within this disclosure refer to both the right brachiocephalic and superior vena cava unless otherwise indicated.

An implantable medical device 80 that may provide a stimulation signal or receive sensed signals to or from the patient's body is implanted subcutaneously. A lead 90 in accordance with the invention is attached to the implantable device 80 and fed into the subclavian vein 40 and from there into the right brachiocephalic 50.

Figure 2:
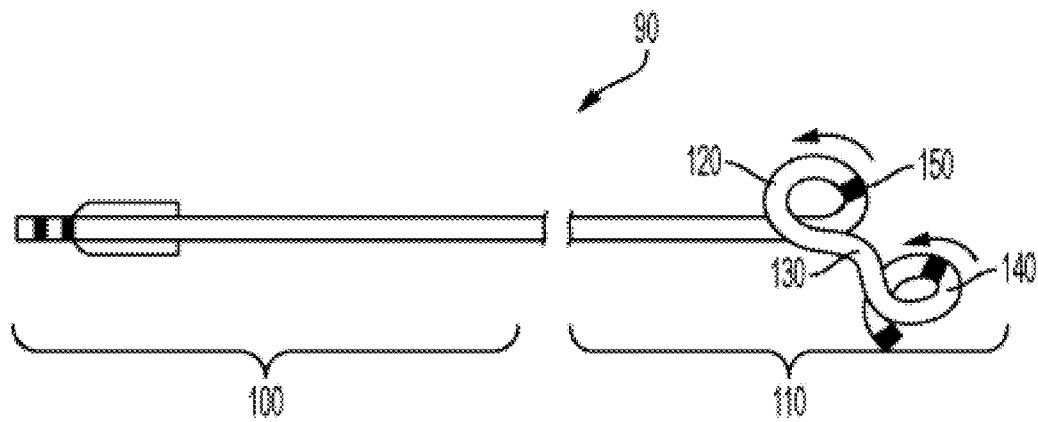
FIG. 2 is a view of a lead in accordance with an embodiment of the invention in an unimplanted condition.

FIG. 2 is a view of a lead in accordance with an embodiment of the invention in an uninstalled condition. Lead 90 has a proximal portion 100 and a distal portion 110. The proximal portion is configured to be connected to an electrical signal generator 80 (not shown). The distal portion 110 includes a stabilizing structure comprising a first loop 120 turning in a first direction, a pre-formed bend 130, and a second loop 140 turning in the same direction as the first loop 120.

The lead 90 may be formed of polyurethane or other biocompatible and suitable material. In some embodiments, the distal portion 110 of the lead may be made more stiff or inflexible to retain preformed biases or for increased durability, for example. The proximal portion may be made more flexible so that it does not exert or transmit excess force to the fixated end of the lead or for other reasons.

In another embodiment in accordance with the invention, a lead similar to the lead of FIG. 2 could be configured so that the second loop 140 turns in the opposite direction of the first loop 120. There is reason to believe that loops turning in opposite directions may be more stable in some applications by reducing the lead's ability to migrate down a lumen. The two loops may "work against" each other during cardiac, respiratory, and limb movement that may induce motion. Lead stability in this area can be challenging because of potential disruptions caused by a patient's coughing, sneezing, deep breathing, or other activities.

The embodiment of FIG. 2 includes at least one electrode 150. The electrode may be a ring electrode, for example, or any electrode known in the art. The electrode is electrically connected to the proximal end 100 of the lead, which is configured to electrically connect the electrode 150 to a signal generator. In the optional embodiment shown in FIG. 2, there is an electrode on the first loop 120, one on the second loop 140, and one at the distal end of the lead.

In its unimplanted condition, this embodiment is generally formed of two dimensional structures (loops, bends) formed in essentially the same plane. From a lead fabrication perspective, it is often simpler to fabricate a "two-dimensional" lead consistently than to fabricate leads that require three-dimensional structures (spirals, biases in more than one plane, etc.). The construction of leads with preformed shapes, such as biases, loops, or bends, can be a complicated and imperfect process, especially considering the small size and relatively delicate nature of many of the lead elements.

In a typical fabrication process for a lead having preformed biases, the lead is held in a particular position by a rod or shaping mandrel placed within lumen of the lead or by other means to retain the lead. The lead is then heated and cooled in this position to form the bend, loop, spiral, or other bias. The resulting shape of the lead formed by this process is different than the shape of the rod or retention device. The lead itself will revert somewhat to its original shape or otherwise respond a bit unpredictably to this and similar biasing processes, in part due to the inherent shape memory of standard materials used to fabricate leads. A lead configured with generally two-dimensional features reacts more predictably and can be reproduced more consistently because there are fewer variables to control. While this invention contemplates and includes "three dimensional" lead designs, it is believed that there are cost and quality benefits to using two-dimensional structures when possible.

Figure 3:
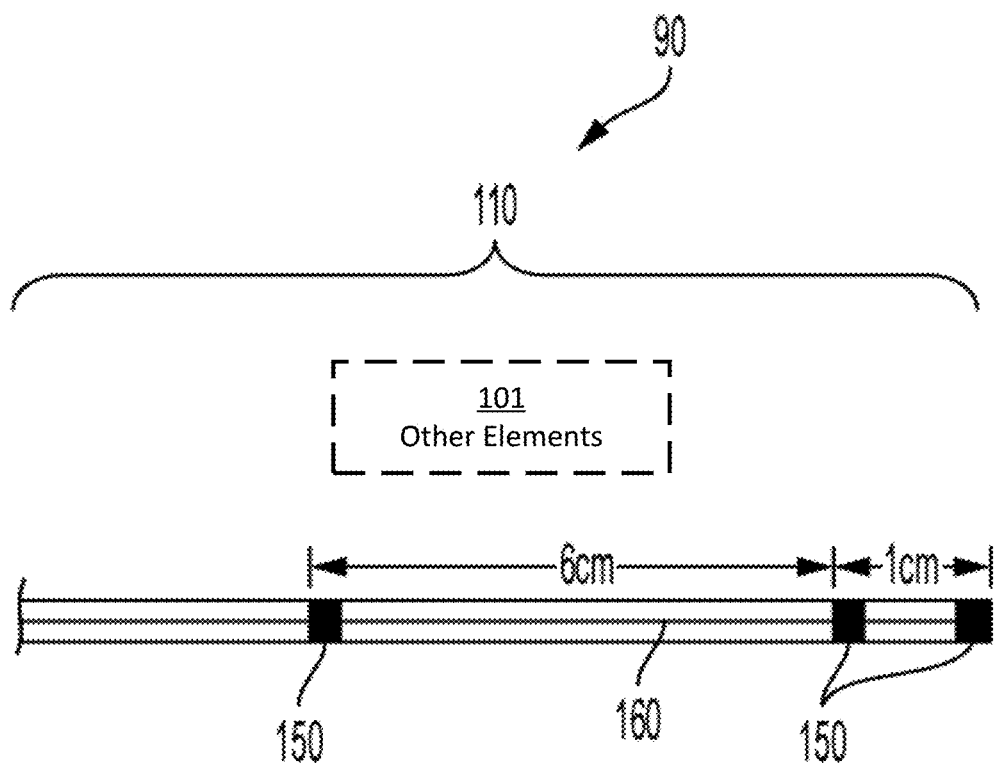
FIG. 3 is a view of a lead in accordance with an embodiment of the invention.

FIG. 3 is a view of a lead in accordance with an embodiment of the invention. The lead in FIG. 3 is forced into a generally straight position by a guide wire or stylet 160 installed within a lumen of the lead body. A first electrode of this embodiment is located at the distal end of the lead body. A second or middle electrode is approximately one centimeter from the distal end of the lead body, and a third electrode is approximately seven centimeters from the end of the lead body (or 6 cm from the middle electrode). This lead is but one example of a lead in accordance with embodiments of the invention, but the dimensions may be representative of a usable lead.

Figure 4:
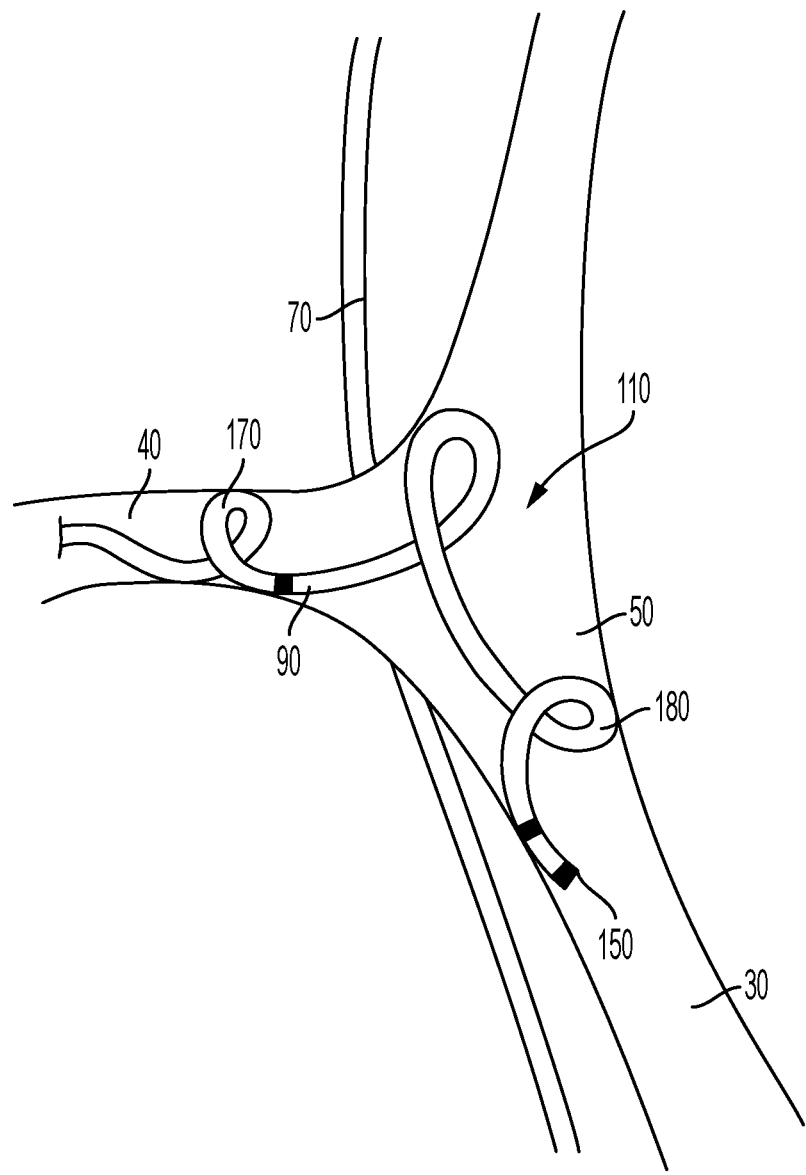
FIG. 4 is a schematic representation of a lead in accordance with embodiments of the invention implanted at the junction of a patient's subclavian vein and right brachiocephalic vein.

FIG. 4 is a schematic representation of a lead in accordance with embodiments of the invention implanted at the junction of a patient's subclavian vein and right brachiocephalic vein. The patient's phrenic nerve 70 runs proximate the junction of the subclavian vein 40 and the right brachiocephalic 50 vein.

The lead 90, as deployed, has distal portion 110 with a first stabilization element 170 generally located in the subclavian vein 40 and a second stabilization element 180 generally located in the right brachiocephalic vein 50. In alternative embodiments, the lead 90 could be implanted with the first stabilization element 170 in the subclavian vein and the second 180 in the internal jugular vein 60. When implanted in the internal jugular vein 60, the lead may be configured to stimulate the vagus nerve as well as or instead of the phrenic nerve. The lead 90 could also be implanted on the patient's left side, either at the junction of the left brachiocephalic and left subclavian or the left subclavian and left internal jugular vein. In fact, embodiments of leads in accordance with the invention may be suitable for implantation at the junction of any two suitable blood vessels or lumens or at a natural bend or flex point in any lumen.

In this embodiment the stabilization elements are generally spiral-shaped when implanted. In some embodiments in accordance with the invention, the spirals begin as preformed loops, a coil of loops, or another generally two-dimensional structure when the lead is constructed. These loops become spirals or other three-dimensional structures as the lead is deployed in a vein. In other embodiments in accordance with the invention, the lead includes preformed spirals. During installation the stabilization elements 170, 180 are straightened with a stylet, guide wire, catheter or other means while being fed to an appropriate location, and take on a generally spiral shape when deployed in a vein, lumen, or lumens.

For the purposes of this disclosure, a "spiral" is considered a lead body that is longitudinally coiling around a fixed line or axis in a constantly changing series of planes and is regarded as three-dimensional. A lead formed in a loop that circles back upon itself or a lead formed as a tightly wound coil are not, strictly speaking, two-dimensional or planar, but for purposes of this disclosure such structures will be considered and referred to as "two-dimensional." Those of skill in the art will understand the distinction set forth herein.

The lead 90 of this embodiment has a plurality of electrodes 150 disposed on the distal portion 110 of the lead. The stabilization elements 170, 180 serve to stabilize and secure the lead within the vessel as well as to position at least one of the electrodes 150 proximate a vessel wall. Preferentially, an electrode 150 will be positioned near a point where the phrenic nerve passes by to enable effective stimulation or sensing of the nerve. In some embodiments the lead 90 will be configured so that one electrode 150 is positioned proximate the wall of the subclavian vein 40 and another is positioned proximate the wall of the brachiocephalic vein 50 so that bipolar stimulation of the phrenic nerve 70 is possible between the two electrodes with a reasonably low level of native impedance.

The spirals of the stabilization elements 170 and 180 may turn in the same direction as each other or in opposite directions. As discussed above, they may be preformed portions of the lead that are initially configured as two-dimensional loops or three-dimensional spirals. The distal end 110 of the lead may be constructed to be relatively stiffer than the proximal portion to allow for more secure fixation by spirals and/or other retaining means while the more flexible proximal portion may be installed with some level of slack so that minimal force is transmitted through the lead body from the proximal to the distal portion, for example. The distal portion of the lead may be configured with other-elements 101 to improve fixation or ultimate stabilization. These elements 101 may include, but are not limited to, one or more barbs, hooks, bumps, depressions, ridges or other surface irregularity, appropriate chemicals and/or materials and coatings promoting cellular formation such as extracellular matrix.

Figure 5:
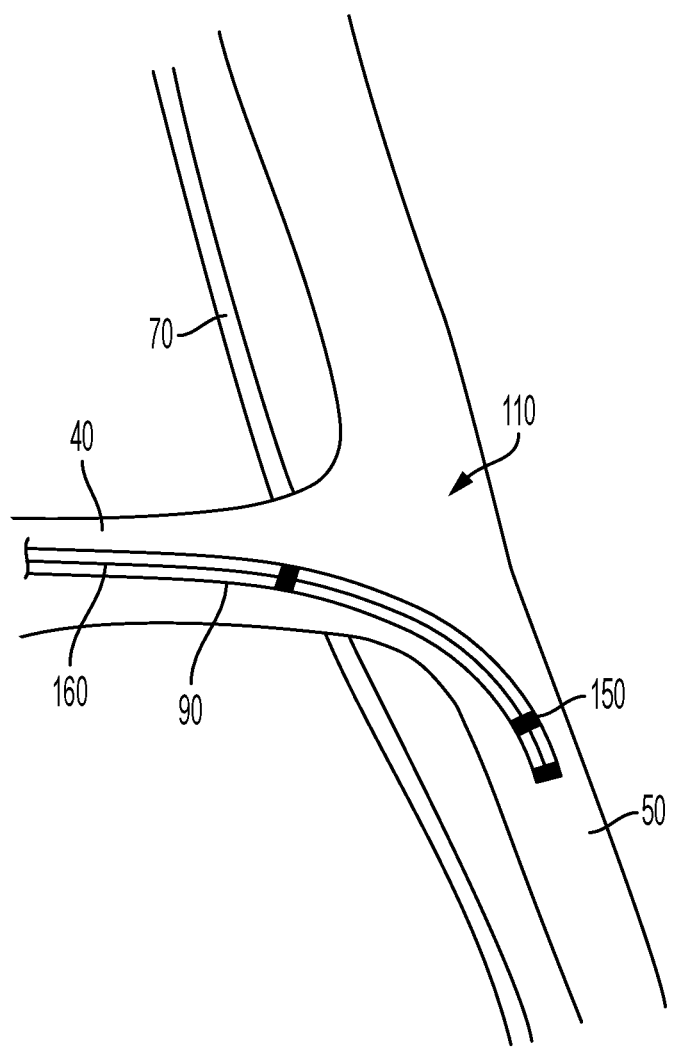
FIG. 5 is a schematic representation of a lead in accordance with embodiments of the invention as it is in the process of being implanted proximate a junction of a patient's subclavian vein and right brachiocephalic vein.

FIG. 5 is a schematic representation of a lead in accordance with, embodiments of the invention as it is in the process of being implanted proximate a junction of a patient's subclavian vein and right brachiocephalic vein. The lead 90 is fed through the subclavian vein 40 into the right brachiocephalic vein 50. The lead has a guide wire or stylet 160 within the lead body and includes at least one electrode 150. Other lead stiffening structures known in the art could be used instead of, or in addition to, the guide wire 160. Despite the presence of the guide wire 160, preformed biases included at the distal end 110 of the lead body still convey a shape to the distal portion 110 of the lead 90. The lead as shown is oriented in the junction of the subclavian vein 40 and the right brachiocephalic 50 in a position that generally conforms to the shape formed by the preformed biases.

Figure 6:
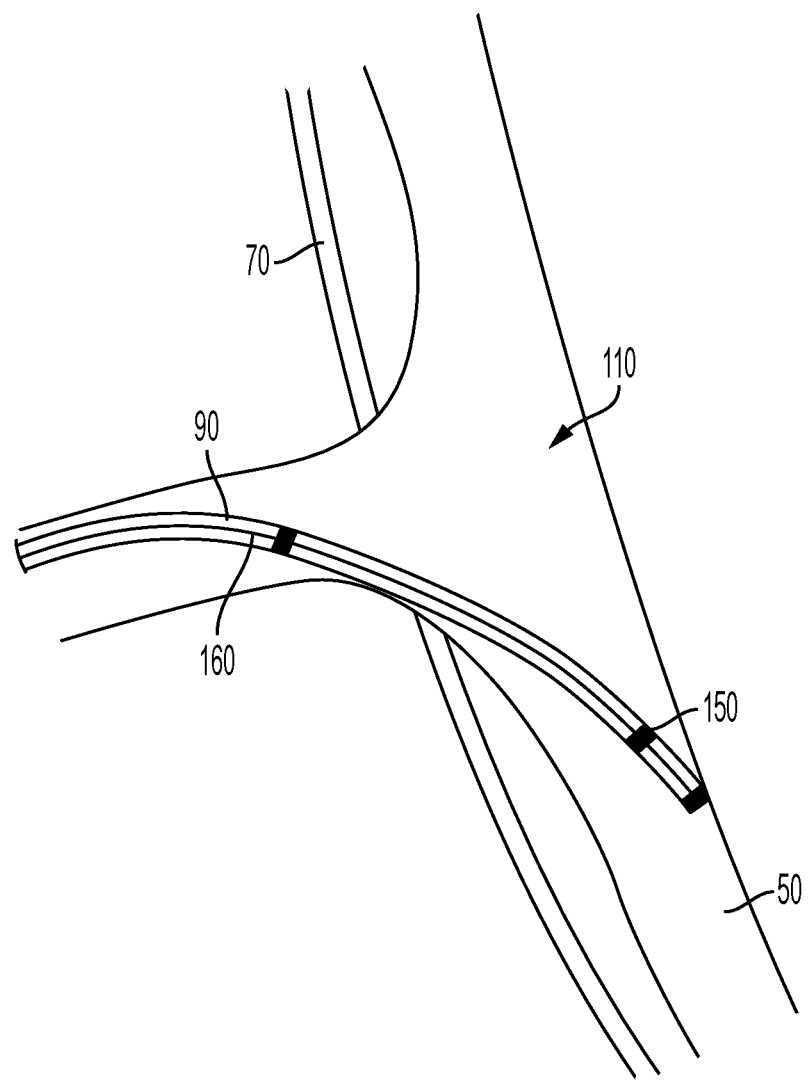
FIG. 6 is a schematic representation of the lead of FIG. 5 as it is in the process of being implanted proximate a junction of a patient's subclavian vein and right brachiocephalic vein.

FIG. 6 is a schematic representation of the lead of FIG. 5 as it is in the process of being implanted proximate a junction of a patient's subclavian vein and right brachiocephalic vein. The lead 90 is fed through the subclavian vein 40 into the right brachiocephalic vein 50. The lead has a guide wire or stylet 160 within the lead body and includes at least one electrode 150. In this representation the lead shape imparted by the lead biases does not conform to the junction of the subclavian vein 40 and the right brachiocephalic vein 50. This position may be referred to as a high potential energy position, and the position represented in FIG. 5 could be referred to as a low potential energy position.

The shape imparted to the lead 90 while on the guide wire or stylet 160 provides for a simple and effective way to assist implanters with optimal positioning of the distal end 110 of the lead 90. The implanter can rotate the lead from a low potential energy position (FIG. 5) to a high potential energy position (FIG. 6). When rotating the lead the implanter will feel increased resistance to rotation as the lead approaches a maximum potential energy position. If the implanter continues to rotate the lead, it will "flip" from a high potential energy position to a low potential energy position. This flipping action provides even more feedback to the implanter regarding the position of the distal end 110 of the lead.

An implantation in accordance with embodiments of the invention may involve an implanter rotating the lead 90 until the implanter can feel the resistance to rotation increasing. As the resistance to rotation approaches the point where the lead will flip from a high potential energy position to a low potential energy position, the implanter holds the lead in place in that high potential energy position and removes the guide wire or stylet. The feedback provided to the implanter allows for a more predictable configuration and orientation of the lead as implanted and increases the likelihood that electrodes disposed on the lead will end up in desirable and effective locations.

In another implantation in accordance with embodiments of the invention, an implanter rotates the lead to a low potential energy position, perhaps just after a flip from a high potential energy position, and removes the guide wire while holding the lead in that position. The principle is the same. The fact that these various positions of the distal end 110 of the lead detectable by an implanter allows a lead designer to design leads and implantation procedures that improve the outcome of the procedure and the effectiveness of any therapy delivery electrodes.

The shape of the distal portion of the lead may be imparted by preformed biases in the lead as described above or by a biased, shaped, or bent guide wire or stylet inserted within a lumen in the lead body. A lead designer may coordinate the design of the stylet and the lead so that the shape creates the same kind of high and low potential energy positions for the stylet/lead combination and provides for similar improvements in lead implantation.

Figure 7:
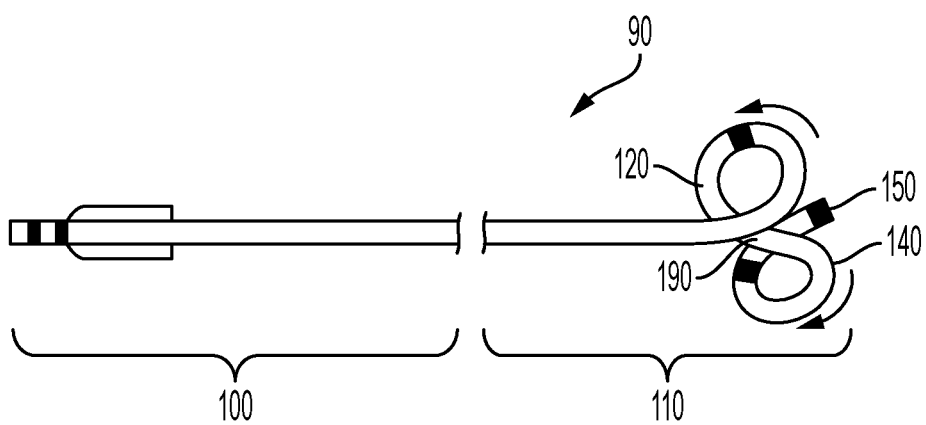
FIG. 7 is a view of a lead in accordance with an embodiment of the invention in an uninstalled condition.

FIG. 7 is a view of a lead in accordance with an embodiment of the invention in an unimplanted condition. Lead 90 has a proximal portion 100 and a distal portion 110. The proximal portion is configured to be connected to an electrical signal generator 80 (not shown). The distal portion 110 includes a stabilizing structure comprising a first loop 120 turning in a first direction, and a second loop 140 turning in the opposite direction from the first loop 120. The transition 190 from the loop 120 turning in one direction to the loop 140 turning in the opposite direction may act as a stabilizing feature as may the bend 130 of the lead shown in FIG. 2. This stabilizing feature may help impart a shape to the lead that assists an implanter with orienting the distal end 110 of the lead during implantation. The stabilizing feature may also act as a secondary fixation element. The leads of FIGS. 2 and 7 may be primarily retained by the loops that generally become spirals upon implantation within a lumen. However, in cases where the leads are implanted at the junction of two vessels, the transition 190 or bend 130 may be designed to conform generally to the shape of the junction and provide a secondary fixation feature.

As an example only, the diameter of the first loop 120 may be between about 16 and 20 mm and the diameter of the second loop 140 may be between about 10 and 15 mm. These dimensions may vary based on patient size, vessel size, implant location, and other considerations, and are provided here only as examples. By understanding how the lead will react in the implant site when properly positioned, lead designers can optimize such variables as loop size and electrode location to increase the likelihood of effective and stable positioning of electrodes.

As mentioned above, some leads in accordance with embodiments of the invention impart shapes to guide wires and other stiffening members when being implanted. This property can assist implanters in orienting the lead, and allows secondary stabilizing features like the bend 130 or transition 190 or others that will occur to those of skill in the art to be more effective.

Figure 8:
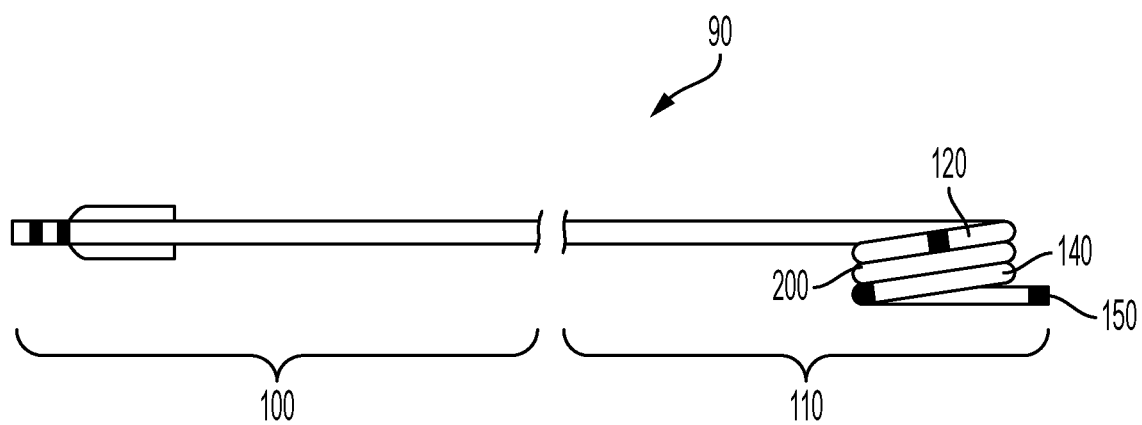
FIG. 8 is a view of a lead in accordance with an embodiment of the invention.

FIG. 8 is a view of a lead in accordance with an embodiment of the invention. Lead 90 has a proximal portion 100 and a distal portion 110. The proximal portion is configured to be connected to an electrical signal generator 80 (not shown). The distal portion 110 includes a stabilizing structure comprising a first loop 120 turning in a first direction, and a second loop 140 turning in the same direction as the first loop 120. The transition 200 from the loop 120 to the second loop 140 turning may act as a stabilizing feature if the lead is implanted at the junction of two lumens. This stabilizing feature may help impart a shape to the lead that assists an implanter with orienting the distal end 110 of the lead during implantation. The stabilizing feature may also act as a secondary fixation element.

One skilled in the art will appreciate that the invention can be practiced with embodiments other than those disclosed. The disclosed embodiments are presented for purposes of illustration and not limitation, and the invention is limited only by the claims that follow.

What is claimed is:

1. A medical electrical lead for implanting in a patient, comprising:
a lead body comprising:
a proximal portion configured to be connected to an implantable medical device comprising an electrical signal generator, and
a distal portion, the distal portion having a spiral shape with a plurality of isodiametric loops, wherein the plurality of isodiametric loops have a diameter based on a blood vessel size and implant location, the plurality of isodiametric loops being configured to stabilize the distal portion when implanted in at least one blood vessel of the patient, wherein the at least one blood vessel of the patient comprises at least one of a brachiocephalic vein, a superior vena cava, or a subclavian vein, the blood vessel size is a size of the at least one blood vessel, and the implant location is a portion of the at least one blood vessel proximate to a phrenic nerve; and
a plurality of electrodes disposed on the distal portion and electrically connected to the electrical signal generator via the lead body.

2. The medical electrical lead of claim 1, comprising a guide wire or stylet configured to be removably installed within the lead body and to be removed from the lead body after the medical electrical lead is implanted in the at least one blood vessel.

3. The medical electrical lead of claim 2, wherein the lead body is configured to:
straighten when the guide wire or stylet is removably installed, and
resume the spiral shape when the guide wire or stylet is removed.

4. The medical electrical lead of claim 1, wherein the lead body comprises polyurethane.

5. The medical electrical lead of claim 1, wherein the plurality of isodiametric loops comprises:
at least a first loop and a second loop, wherein the first loop and the second loop turn in a same direction.

6. The medical electrical lead of claim 5,
wherein at least one first electrode of the plurality of electrodes is disposed on the first loop, and
wherein at least one second electrode of the plurality of electrodes is disposed on the second loop.

7. The medical electrical lead of claim 6, wherein none of the plurality of electrodes is disposed on a transition between the first loop and the second loop.

8. The medical electrical lead of claim 5, wherein at least one electrode of the plurality of electrodes is disposed at a distal end of the distal portion.

9. The medical electrical lead of claim 1, wherein the lead body is configured to pass through a subclavian vein to enter a brachiocephalic vein or a superior vena cava.

10. The medical electrical lead of claim 1, wherein the implantable medical device is configured to receive sensed signals from the patient's body.

11. The medical electrical lead of claim 1, wherein the distal portion comprises one or more fixation elements.

12. The medical electrical lead of claim 11, wherein the one or more fixation elements comprise one or more of a barb, a hook, a bump, a depression, or a ridge.

13. The medical electrical lead of claim 11, wherein the one or more fixation elements comprise one or more of a material coating or a chemical coating.

14. The medical electrical lead of claim 1, wherein the phrenic nerve is a right phrenic nerve.

15. The medical electrical lead of claim 1, wherein the phrenic nerve is a left phrenic nerve.

* * * * *